United States Patent [19]
Sabb et al.

[11] Patent Number: 5,750,522
[45] Date of Patent: May 12, 1998

[54] PYRROLO[1,2-D] [1,2,4]TRIAZINE DERIVATIVES

[75] Inventors: Annmarie Louise Sabb, Pennington, N.J.; William A. Kinney, Churchville, Pa.

[73] Assignee: American Home Products Corporation, Madison, N.J.

[21] Appl. No.: 678,851

[22] Filed: Jul. 12, 1996

Related U.S. Application Data

[60] Provisional application No. 60/001,125 Jul. 13, 1995.
[51] Int. Cl.[6] .................. C07D 253/10; A61K 31/53
[52] U.S. Cl. ........................................ 514/243; 544/183
[58] Field of Search ........................... 514/243; 544/183

[56] References Cited

FOREIGN PATENT DOCUMENTS

WO9113885  9/1991  WIPO.

OTHER PUBLICATIONS

Lancelot, J-C. et al. *J. Heterocyclic Chem.*, 17:631–635 (Jun. 1980).

*Primary Examiner*—John M. Ford
*Attorney, Agent, or Firm*—Arnold S. Milowsky

[57] ABSTRACT

This invention provides compounds having the formula

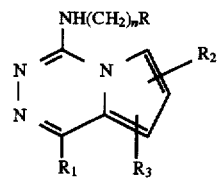

wherein

R is azacycle or azabicycle;

$R_1$ is alkyl;

$R_2$ and $R_3$ are each, independently, hydrogen, alkyl, alkoxy, or thioalkyl;

n is 0–5;

or a pharmaceutically acceptable salt thereof, which are useful in treating symptoms of cholinergic insufficiency involving cognitive disorders.

15 Claims, No Drawings

PYRROLO[1,2-D] [1,2,4]TRIAZINE DERIVATIVES

BACKGROUND OF THE INVENTION

This application claims the benefit of U.S. Provisional Application No. 60/001,125, filed Jul. 13, 1995.

Cognitive disorders have many components including forgetfulness, confusion, memory loss, attention deficits, and deficits in visual perception. Some of the symptoms of cognitive disorders are associated with decreased levels of the neurotransmitter, acetylcholine. Neurological illnesses related to cholinergic deficiency include presenile dementia and senile dementia of the Alzheimer's type (SDAT), Parkinson's disease, Down's syndrome, and dementia pugilistica.

The "cholinergic hypothesis" [R. T. Bartus, et al., Science, 217, 408–417 (Jul. 30, 1982)] suggests that memory loss due to decreased levels of acetylcholine can be ameliorated by correcting the levels of acetylcholine in the brain using an acetylcholine releasing agent, an acetylcholine esterase inhibitor, or by using a drug which mimics acetylcholine (cholinomimetic). Marketing of the acetylcholine esterase inhibitor, tacrine, has demonstrated that improvement in memory can be shown in patients with mild to moderate Alzheimer's disease [M. Williams, Curr. Opin. Invest. Drugs, 2(5), 541–544 (May 1993)]. The utility of this drug is limited, however, because of adverse side effects especially at the higher doses where it is most effective. Clinical studies using the natural alkaloid, arecoline, a cholinergic agonist, have also demonstrated memory improvement in patients with mild to moderate Alzheimer's disease. Because of the short half-life of arecoline, the clinical study was done using continuous infusion of the drug over a 2 week period. In addition, a peripheral muscarinic antagonist, N-methylscopolamine, was also administered during the study to prevent potential autonomic side effects. [T. T. Soncrant et al., Psychopharmacology, 112, 421–427 (1993)].

Cholinergic receptors which bind to and are activated by the alkaloid, muscarine, are called muscarinic receptors. Three pharmacologically defined subtypes of muscarinic receptors have been identified. They are referred to as M1, M2, and M3 based upon their affinity for the M1 antagonist, pirenzepine, the M2 antagonist, AFDX-116, and the M3 antagonist, 4-[(diphenylacetyl)oxy]-1,1-dimethylpiperidinium iodide (4-DAMP). Five different human muscarinic receptors have been cloned. The Hm1 (human m1) receptor is found primarily in the frontal cortex. [T. I. Bonner, Trends in Pharmacological Sciences, supplement, Jul. 20–27 (1989) p11–15,]. Activation of the m1 receptor results in an increase in phosphoinositol hydrolysis (PI turnover).[K. Fukuda, et al., Ibid, p. 4–10]. Carbachol, like muscarine, is able to fully activate m1 receptors. These two compounds, however, contain a quaternary ammonium group and as a result are not able to enter the CNS. Compounds of this invention do not contain a quaternary ammonium group.

DESCRIPTION OF THE INVENTION

This invention provides pyrrolo(1,2-d)(1,2,4)triazines which are able to bind to and stimulate central muscarinic acetylcholine receptors and are useful agents for treating symptoms of cholinergic insufficiency involving cognitive disorders, specifically the impaired memory associated with a decrease in the neurotransmitter, acetylcholine. The compounds of the present invention have the formula

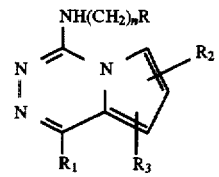

wherein

R is azacycle or azabicycle;

$R_1$ is alkyl of 1–6 carbon atoms;

$R_2$ and $R_3$ are each, independently, hydrogen, alkyl of 1–6 carbon atoms, alkoxy of 1–6 carbon atoms, or thioalkyl of 1–6 carbon atoms;

n is 0–5;

or a pharmaceutically acceptable salt thereof.

The pharmaceutically acceptable salts are those derived from organic and inorganic acids such as: acetic, lactic, citric, tartaric, succinic, maleic, malonic, gluconic, hydrochloric, hydrobromic, phosphoric, nitric, sulfuric, methanesulfonic, and similarly known acceptable acids.

Azacycle is defined as a saturated heterocycle having one nitrogen and preferably 3–6 carbon atoms. Azabicycle is defined as a saturated bridged bicycloheterocycle having one nitrogen. It is preferred that the azabicycle contains 5–8 carbon atoms.

The preferred compounds of the present invention are those in which R is 3-azabicyclo[3.2.2]nonane or 3-azabicyclo[2.2.2]octane; those in which R is 3-azabicyclo [3.2.2]nonane or 3-azabicyclo[2.2.2]octane and $R_1$ is alkyl of 1–3 carbon atoms; those in which R is 3-azabicyclo[3.2.2] nonane or 3-azabicyclo[2.2.2]octane and $R_1$ methyl; and those in which R is 3-azabicyclo[3.2.2]nonane or 3-azabicyclo[2.2.2]octane, $R_1$ is alkyl of 1–3 carbon atoms, and n is 0–4.

Some of these compounds may exist as racemates or enantiomers and are prepared by the general synthetic methods detailed in Scheme I and are identified as compound VI. This invention covers such racemates and enantiomers.

SCHEME I

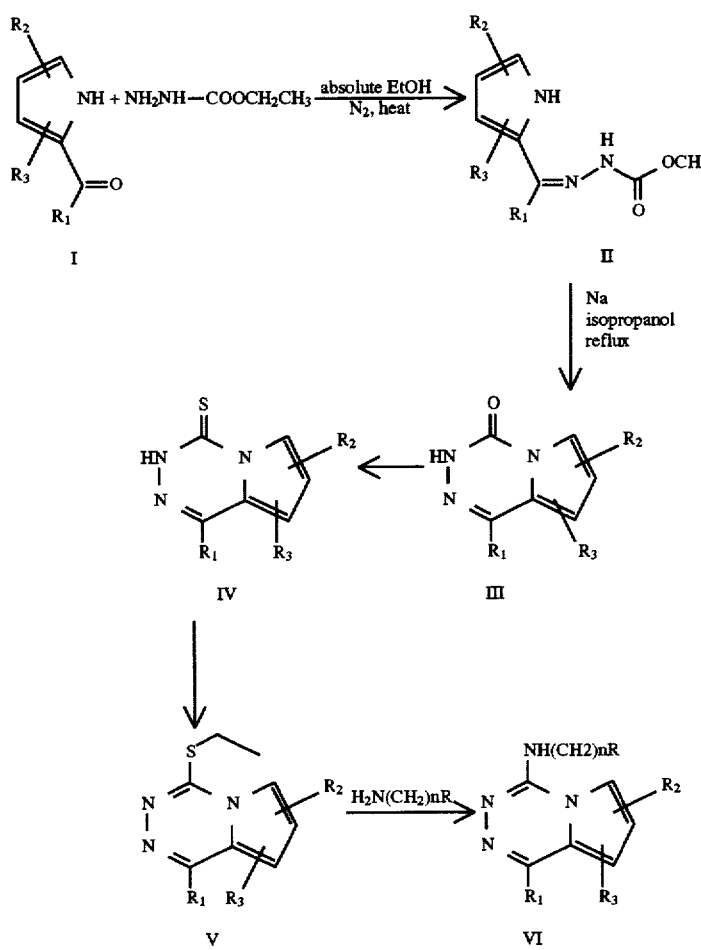

Referring to Scheme I, the requisite 2-acylpyrrole I is allowed to react with a hydrazinoalkylcarboxylate in an organic solvent, such as absolute ethanol under a nitrogen atmosphere at elevated temperatures to give the corresponding hydrazones II. Treatment of the pyrrolo-hydrazones II with a metal, such as sodium, in a polar solvent, such as 2-propanol, under an inert atmosphere, such as a nitrogen atmosphere, at elevated temperatures forms 5-alkylpyrrolo (1,2-d)(1,2,4)triazin-2-ones III.[Lancelot, J-C; Maume, D., Robba, M. *J. Heterocyclic Chem.* 17, 631 (1980).] Heating a mixture of a pyrrolo(1,2-d)1,2,4)trazin-2-one III and a sulfurating agent, such as Lawsson's reagent, in an organic solvent, such as toluene, under an inert atmosphere, such as a nitrogen atmosphere, gives the corresponding 5-alkylpyrrolo(1,2-d)(1,2,4)triazin-2-thione IV. Alkylation of the thione using an alkylating agent such as an alkyl halide, in an organic solvent, such as tetrahydrofuran (THF), at elevated temperatures, in the presence of an inorganic salt, such as cesium carbonate, gives 5-alkyl-2-alkylthiopyrrolo (1,2-d)(1,2,4)triazines V. Heating a mixture of the 5-alkyl-2-alkylthiopyrrolo(1,2-d)(1,2,4)triazines V with amines gives products of this invention VI.

The affinity of the compounds of this invention for muscarinic receptors was established by testing them in accordance with the standard pharmacological test procedures in which the compound's ability to compete with [$^3$H]QNB binding and by analysis of PI hydrolysis stimulation in accordance with the following procedures:

The binding affinity of the compounds of this invention at muscarinic receptor subtypes was determined by incubating triplicate samples of homogenized Chinese Hamster Ovary (CHO) cells which had been transfected with CMV vector containing cDNA expressing individual muscarinic receptor subtypes, for one hour at 37° C. with 0.23 nM radiolabeled quinuclidinyl benzilate [$^3$H]QNB, a representative compound of this invention, and a volume of 10 mM phosphate buffer to obtain a final incubation volume of 1000 μL. Vehicle and 2 μM atropine sulfate are substituted for the test solution to determine total and non-specific bindings, respectively. After incubation, the solutions are filtered and the filter paper is subjected to scintillation spectroscopy for radioactivity counting. Specific binding in the presence of the compound of this invention is expressed as a percentage of the atropine-sensitive binding. A concentration-response evaluation is obtained through non-linear regression analysis to obtain an $IC_{50}$ and/or $K_i$ value. This procedure is based on that of Tonnaer et al. *Life Sci.*, 40, 1981 (1987).

The ability of the compounds of this invention to stimulate hydrolysis of phosphoinositide (PI) in chinese Hamster Ovary (CHO) cells which had been transfected with CMV vector containing CDNA expressing $M_1$ acetylcholine receptors was determined in accordance with the procedure of El-Fakahany et al. *J. Pharmacol. Exp. Ther.* 257, 938 (1991), whereby PI hydrolysis is performed in reaction tubes, each containing 880 μL Kreb's Buffer, 10 μL of 1.0M LiCl solution, 10 μL of the compound representative of this invention or control vehicle, and 100 μL of CHO cell suspension in Kreb's Buffer (1,000,000 cells per mL). The tubes are incubated for one hour at 37° C. The reaction is quenched with chloroform and the phosphatidyl inositols are extracted with methanol and chloroform. Phase separation is assured with the addition of methanol and water followed by centrifugation. The tritiated inositol phosphates are recovered on BioRad AG 1-X8 anion exchange resin in the formate cycle. After washing the resin with water and myo-inositol, the inositol phosphates are eluted with ammonium formate/formic acid, collected and subjected to liquid scintillation spectroscopy. The results are expressed as a percentage of the mean value obtained for carbachol ($EC_{50}$= 8.0 μM).

The results of these studies are given below:

IN VITRO PHARMACOLOGY

| Compound # | ml $^3$H QNB Binding in CHO cells Ki (μM) | % PI Hydrolysis ml receptors in CHO cells 30x Ki (μM) carb = 100% |
|---|---|---|
| Example 1 | 0.31 | |
| Example 2 | 1.39 | |
| Example 3 | 4.45 | 24 |
| Example 4 | 20.18 ($IC_{50}$) | |

Hence, the compounds of this invention demonstrated high affinity for muscarinic receptors (especially the ml receptor) and are therefore useful in the treatment of disease states associated with insufficient cerebral acetylcholine production or release.

Based upon this receptor binding information and PI hydrolysis, the compounds of this invention are characterized as useful in the treatment of cognitive disorders associated with decreased levels of cerebral acetylcholine production or release, such as presenile dementia, senile dementia of the Alzheimer's type, Parkinson's disease, Down's syndrome and dementia pugilitica.

As such, the compounds may be administered neat or with a pharmaceutical carrier to a patient in need thereof. The pharmaceutical carrier may be solid or liquid.

Applicable solid carriers can include one or more substances which may also act as flavoring agents, lubricants, solubilizers, suspending agents, fillers, glidants, compression aids, binders or tablet-disintegrating agents or an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. Oral administration may be either liquid or solid composition form.

The dosage requirements vary with the particular compositions employed, the route of administration, the severity of the symptoms presented and the particular subject being treated. The dosage to be used in the treatment of a specific patient suffering from cerebral acetylcholine insufficiency must be subjectively determined by the attending physician. The variables involved include the severity of the dysfunction, and the size, age and response pattern of the patient. The dosage to be used in the treatment of a specific patient suffering from cerebral acetylcholine insufficiency must be subjectively determined by the attending physician. The variables involved include the severity of the dysfunction, and the size, age, and response of the patient. Based on the results obtained in the standard pharmacological test procedures, projected daily intravenous dosages would be 0.001–50 mg/kg. Projected daily oral dosages would be 0.01–100 mg/kg.

Preferably the pharmaceutical composition is in unit dosage form, e.g. as tablets or capsules. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form.

The following shows the preparation of representative compounds of this invention and are presented for illustrative purposes only that are not to be construed as limitations for the disclosed invention. Those skilled in the art will be aware of other methods of preparing compounds of this invention. The starting materials or intermediates are available commercially or can be prepared by standard literature procedures.

EXAMPLE 1

[4-(3-Azabicyclo[3.2.2]-3-yl)-butyl]-(1-methylpyrrolo[1,2-d][1,2,4]triazin-4-yl)amine dihydrochloride 2-Acetylpyrrole (3.31 g, 30.37 mmol) and ethyl hydrazinecarboxylate (3.47 g, 33.41 mmol) in absolute ethanol (150 mL) were heated under reflux in a nitrogen atmosphere for 48 hours. The solvent was removed on a rotary evaporator and the residue was purified by high pressure liquid chromatography (HPLC) on silica gel eluting with 80:20 methylene chloride:acetonitrile. 2-[1-(2-pyrrole)ethylidene]-hydrazinecarboxylic acid ethyl ester (VII, 5.2 g, 87.8%) was obtained as a white solid: m.p.73°–74° C.

Elemental analysis for $C_9H_{13}N_3O_2$ Calc'd: C, 55.37; H, 6.71 N, 21.52 Found: C, 55.36; H, 6.64; N, 21.79

Sodium (5.5 g, 0.23 m) was dissolved in n-propanol (300 mL). A solution of VII (39.56 g, 0.203 m) in n-propanol (300 mL) was added and the reaction mixture was heated under reflux for 4 hours in a nitrogen atmosphere. The reaction mixture was allowed to cool to room temperature and adjusted to pH 1 with 1M HCl. The aqueous phase was extracted with methylene chloride (2 times). The organic phases were combined and washed with water, dried over $MgSO_4$ and rotary evaporated to give 5-methylpyrrolo[1,2-d][1,2,4]triazin-2-one (VIII, 27.41 g, 90.6%).

A suspension of triazin-2-one VIII (18.46 g, 0.124 m) and Lawsson's reagent (50.46 g, 0.125 m) in anhydrous toluene (1450 mL) was heated under reflux in a nitrogen atmosphere for 3 hours. After cooling the reaction mixture to room temperature the toluene was removed on a rotary evaporator. The residue was suspended in ethyl acetate (800 mL) and filtered to separate insoluble materials. The filtrate was rotary evaporated and the residue was purified by HPLC on silica gel eluting with methylene chloride containing a gradient of methanol, to give 16.54 g of partially purified product. Recrystallization from ethyl acetate gave 5-methylpyrrolo[1,2-d][1,2,4]triazin-2-thione (IX 12.16 g, 59%) as a white solid, m.p.: 205°–208° C.

Elemental analysis for $C_7H_7N_3S$ Calc'd: C, 50.89; H, 4.27; N, 25.43 Found: C, 50.86; H, 4.22; N, 25.81

A suspension of cesium carbonate (1.0 g, 0.0031 m) in THF (20 mL) containing triazin-2-thione IX (0.5 g, 0.0030 m) was treated with ethyl iodide (0.96 g, 0.0061 m) and heated under reflux overnight. After cooling to room temperature, the reaction mixture was diluted with methylene chloride and filtered through Celite. The filtrate was evaporated and the residue was purified by column chromatography on silica gel eluting with methylene chloride containing 5–10% acetonitrile. 2-Thioethyl-5-methylpyrrolo[1,2,-d][1,2,4]triazine (X 0.27 g, 47%) was obtained as an oil.

A mixture of 2-thioethyl-5-methylpyrrolo[1,2-d][1,2,4] triazine X (0.72 g, 0.0037 m) and 4-(3-azabicyclo[3.2.2] butylamine (1.41 g, 0.0072 m) was stirred and heated in an oil bath at 110° C. until TLC analysis indicated that there was no remaining starting material (silica gel, 1:1 methanol: methylene chloride containing a drop of concentrated ammonia). The reaction mixture was dissolved in methylene chloride and purified by flash column chromatography on silica gel eluting with methylene chloride containing 10–40% methanol. The free base of the title compound was isolated as an oil (0.68 g, 55%). The oil was dissolved in ether and excess 1.0M HCl in ether (2.6 mL) was added and the sample was stored in a freezer overnight. The HCl salt was isolated by filtration and recrystallized from ethanol containing ether and hexane. After standing in the freezer overnight, the cold mixture was filtered and the crystals were isolated and dried at <1 mm Hg (50°–60° C.) to give the title compound (0.39 g) as a white powder, m.p.: 300°–305° C. (dec).

Elemental analysis for $C_{19}H_{29}N_5.2HCl$ Calc'd: C, 56.99; H, 7.80; N, 17.49 Found: C, 56.61; H, 7.72; N, 17.09

EXAMPLE 2

[4-(3-Azabicyclo[3.2.2.]-3-propyl]-(1-methylpyrrolo [1,2-d][1,2,4]triazin-4-yl)amine dihydrochloride Following the procedure of Example 1, a mixture of 2-thioethyl-5-methylpyrrolo[1,2-d][1,2,4]triazine X (0.70 g, 0.0036 m) and 4-(3-azabicyclo[3.2.2]propylamine (1.55 g, 0.0085 m) was stirred and heated in an oil bath at 120° C. for 6 hours. The free base of the title compound was isolated by flash column chromatography on silica gel eluting with methylene chloride containing methanol 10–100%. The free base was dissolved in ethanol (15–20 mL) and treated with 1M HCl in ether (3.4 mL). After standing overnight in a freezer, the salt was isolated by filtration and recrystallized from ethanol and dried at <1 mm Hg (50°–60° C.) to give 0.30 g of the title compound as a white powder, m.p.: 240° C. (dec.), which was isolated as a hydrate.

Elemental analysis for $C_{18}H_{27}N_5.2HCl.H_2O$ Calc'd: C, 53.46; H, 7.73; N, 17.32 Found: C, 53.44; H, 7.68; N, 17.18

EXAMPLE 3

[4-(3-Azabicyclo[3.2.2]non-3-yl)ethyl]-(1-methylpyrrolo[1,2-d][1,2,4]triazin-4-yl)amine dihydrochloride Following the procedure of Example 1, a mixture of 2-thioethyl-5-methylpyrrolo[1,2-d][1,2,4]triazine X (0.70 g, 0.0036 m) and 4-(3-azabicyclo[3.2.2]ethylamine (1.30 g, 0.0084 m) was stirred and heated in an oil bath at 120° C. for 6 hours. The free base of the title compound was isolated by flash column chromatography on silica gel eluting with methylene chloride containing methanol 10–100%. The free base was dissolved in ethanol (15–20 mL) and treated with 1M HCl in ether (3.4 mL). After standing overnight in a freezer, the salt was isolated by filtration and dried at <1 mm Hg (50–60 C) to give 0.21 g of the title compound as a white powder, m.p.: 250° C. (dec.)

Elemental analysis for $C_{17}H_{25}N_5.2HCl$ Calc'd: C, 54.83; H, 7.31; N, 18.81 Found: C, 54.65; H, 7.21; N, 18.65

EXAMPLE 4

(1-Azabicyclo[2.2.2]oct-3-yl)-1-methylpyrrolo[1,2-d][1,2,4]triazin-4-ylamine dihydrochloride Following the procedure of Example 1, a mixture of 2-thioethyl-5-methylpyrrolo[1,2-d][1,2,4]triazine X (1.51 g, 0.0078 m) and 3-aminoazabicyclo[2.2.2]octane (12.37 g, 0.098 m) was stirred and heated in an oil bath at 112° C. for 36 hours. The reaction mixture was partitioned between water and ethyl acetate. The aqueous phase was saturated with sodium chloride and extracted with ethyl acetate (2 times). The organic layers were combined, dried ($MgSO_4$), and evaporated to give a residue which was purified by HPLC on silica gel eluting with methylene chloride containing a gradient of methanol. The free base was dissolved in ethanol and treated with ethereal HCl to form the title compound (0.43 g), m.p.: 255° C. (dec.).

Elemental analysis for $C_{14}H_{19}N_5.2HCl$ Calc'd: C, 50.91; H, 6.41; N, 21.21 Found: C, 50.69; H, 6.40; N, 20.89

What is claimed is:

1. A compound having the formula

wherein

R is a saturated heterocycle having one nitrogen and 3–6 carbon atoms or a saturated bridged bicycloheterocycle of 5–8 carbon atoms having one nitrogen;

$R_1$ is alkyl of 1–6 carbon atoms;

$R_2$ and $R_3$ are each, independently, hydrogen, alkyl of 1–6 carbon atoms, alkoxy of 1–6 carbon atoms, or thioalkyl of 1–6 carbon atoms;

n is 0–5;

or a pharmaceutically acceptable salt thereof.

2. The compound according to claim 1, wherein R is a saturated bridged bicycloheterocycle of 5–8 carbon atoms having one nitrogen or a pharmaceutically acceptable salt thereof.

3. The compound of claim 2 wherein the the saturated bridged bicycloheterocycle of 5–8 carbon atoms having one nitrogen is 3-azabicyclo[3.2.2]nonane or 3-azabicyclo[2.2.2]octane or a pharmaceutically acceptable salt thereof.

4. The compound of claim 3, wherein $R_1$ is alkyl of 1–3 carbon atoms or a pharmaceutically acceptable salt thereof.

5. The compound of claim 4, wherein n=0–4 or a pharmaceutically acceptable salt thereof.

6. The compound of claim 1, which is [4-(3-azabicyclo[3.2.2]-3-yl)-butyl]-(1-methylpyrrolo[1,2-d][1,2,4]triazin-4-yl)amine or a pharmaceutically acceptable salt thereof.

7. The compound of claim 1, which is [4-(3-azabicyclo[3.2.2]-3-yl)-butyl]-(1-methylpyrrolo[1,2-d][1,2,4]triazin-4-yl)amine dihydrochloride.

8. The compound of claim 1, which is 4-(3-azabicyclo[3.2.2.]-3-propyl]-(1-methylpyrrolo[1,2-d][1,2,4]triazin-4-yl)amine or a pharmaceutically acceptable salt thereof.

9. The compound of claim 1, which is 4-(3-azabicyclo[3.2.2.]-3-propyl]-(1-methylpyrrolo[1,2-d][1,2,4]triazin-4-yl)amine dihydrochloride.

10. The compound of claim 1, which is [4-(3-azabicyclo[3.2.2]non-3-yl)ethyl]-(1-methylpyrrolo[1,2-d][1,2,4]triazin-4-yl)amine or a pharmaceutically acceptable salt thereof.

11. The compound of claim 1, which is [4-(3-azabicyclo[3.2.2]non-3-yl)ethyl]-(1-methylpyrrolo[1,2-d][1,2,4]triazin-4-yl)amine dihydrochloride.

12. The compound of claim 1, which is (1-azabicyclo[2.2.2]oct-3-yl)-1-methylpyrrolo[1,2-d][1,2,4]triazin-4-ylamine or a pharmaceutically acceptable salt thereof.

13. The compound of claim 1, which is (1-azabicyclo[2.2.2]oct-3-yl)-1-methylpyrrolo[1,2-d][1,2,4]triazin-4-ylamine dihydrochloride.

14. A method of alleviating the symptoms of memory loss attending senility which comprises administering to a patient in need thereof, parenterally or orally, a muscarinic receptor active compound of the formula

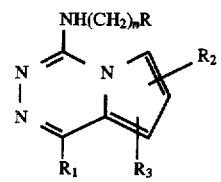

wherein

R is a saturated heterocycle having one nitrogen and 3–6 carbon atoms or a saturated bridged bicycloheterocycle of 5–8 carbon atoms having one nitrogen;

$R_1$ is alkyl of 1–6 carbon atoms;

$R_2$ and $R_3$ are each, independently, hydrogen, alkyl of 1–6 carbon atoms, alkoxy of 1–6 carbon atoms, or thioalkyl of 1–6 carbon atoms;

n is 0–5;

or a pharmaceutically acceptable salt thereof in an amount sufficient to enhance cognition.

15. A pharmaceutical composition which comprises a compound of having the formula

wherein

R is a saturated heterocycle having one nitrogen and 3–6 carbon atoms or a saturated bridged bicycloheterocycle of 5–8 carbon atoms having one nitrogen;

$R_1$ is alkyl of 1–6 carbon atoms;

$R_2$ and $R_3$ are each, independently, hydrogen, alkyl of 1–6 carbon atoms, alkoxy of 1–6 carbon atoms, or thioalkyl of 1–6 carbon atoms;

n is 0–5;

or a pharmaceutically acceptable salt thereof, and a pharmaceutical carrier.

* * * * *